United States Patent [19]

Bailey et al.

[11] Patent Number: 5,182,940
[45] Date of Patent: Feb. 2, 1993

[54] FLASH POINT TESTING APPARATUS AND METHOD

[75] Inventors: Kenneth M. Bailey, Heath; Rex L. Mitchener, Dallas; Timothy J. Wehking, Garland; Craig P. Reith, Seabrook, all of Tex.

[73] Assignee: Automated Pipeline Instruments Incorporated, Heath, Tex.

[21] Appl. No.: 778,006

[22] Filed: Oct. 17, 1991

[51] Int. Cl.$^5$ .......................................... G01N 25/52
[52] U.S. Cl. ...................................... 73/36; 73/61.41; 374/8; 374/142
[58] Field of Search .................. 374/8, 142; 73/36, 35

[56] References Cited

U.S. PATENT DOCUMENTS

| | | | |
|---|---|---|---|
| 2,752,776 | 7/1956 | Kapff et al. | 73/35 X |
| 3,293,904 | 12/1966 | Ratway et al. | 73/36 |
| 3,293,905 | 12/1966 | Ratway et al. | 73/36 |
| 4,348,117 | 9/1982 | Michels | 374/27 X |
| 4,831,559 | 5/1989 | Miller | 374/8 X |

Primary Examiner—Daniel M. Yasich
Attorney, Agent, or Firm—W. Kirk McCord

[57] ABSTRACT

Apparatus is provided for continually monitoring the flash point temperature of a liquid petroleum product flowing through a pipeline. The apparatus is located adjacent the pipeline for periodically drawing product samples therefrom and for testing the samples to determine the respective flash point temperatures. The apparatus includes a microprocessor, which is programmed to control the operation of the apparatus, a testing chamber and a Wheatstone bridge circuit for measuring the Lower Explosive Limit (LEL) of a combustible gas-air mixture which is drawn through the testing chamber. The gas-air mixture ignites on the surface of an active resistive filament, thereby increasing its temperature and resistance, which causes a current to flow within the magnitude bridge circuit. The magnitude of the current is directly proportional to the change of resistance of the active filament and the LEL of the vapor-air mixture. The microprocessor computes the flash point temperature of the sample based on the measured LEL and on the temperature and API gravity of the liquid sample. A backup Wheatstone bridge circuit is provided in the event of failure or degradation of the primary active filament. The microprocessor automatically switches to the backup bridge circuit in the event of a malfunction of the primary bridge circuit.

18 Claims, 12 Drawing Sheets

FLASH POINT TESTING APPARATUS AND METHOD

FIELD OF INVENTION

This invention relates generally to petroleum products and in particular to an improved apparatus and method for monitoring the flash point of a pipeline-transported petroleum product.

BACKGROUND OF THE INVENTION

The "flash point" of a liquid petroleum product is typically defined as the lowest temperature at which the application of a test flame causes the vapor emitted from the liquid to ignite. The flash point typically will be different for different petroleum products. Flash point is an important parameter in determining whether refined fuel oils are suitable for use. Each type of fuel oil, including gasoline, kerosine, and certain types of aircraft fuel, has an established range of acceptable flash points. (If the flash point is below the minimum acceptable level, the product may cause damage to combustion engines. On the other hand, if the flash point is above the maximum acceptable level, the product may not be usable for its intended purpose.)

Typically, refined fuel oils are transported by means of an oil pipeline from an oil refinery to a network of tank farms for temporary storage prior to distribution. Pipelines are normally designated for certain types of fuels. The flash point of the fuel oil product being transported through the pipelines should be monitored periodically to ensure that the product is suitable for distribution and subsequent use.

DESCRIPTION OF THE PRIOR ART

According to prior practice, flash point is determined by periodically taking a sample of the product from the pipeline and testing the sample in a laboratory to determine its flash point. Established methods of laboratory testing include the so-called "Tag Closed Cup" testing method in which a product sample is heated at a constant rate and a small flame is applied to the sample at regular intervals. Flash point is determined to be the lowest temperature at which the application of the test flame causes the vapor above the liquid sample to ignite. The process is relatively time consuming (i.e., 15 to 20 minutes per sample) and requires a human operator to draw the sample and deliver it to the laboratory for testing.

Another method of flash point testing known in the art is the so-called "Pensky-Martens Closed Cup" method. This method is similar to the Tag Closed Cup method, described above. The liquid sample is heated at a slow, constant rate with continual stirring. A small flame is applied to the sample at regular intervals with simultaneous interruption of the stirring. The flash point is determined to be the lowest temperature at which the application of the test flame causes the vapor above the liquid sample to ignite. This method is also relatively slow (i.e., 10 to 15 minutes per sample) and also requires a human operator to draw the sample and deliver it to the laboratory for testing.

Devices are also available for testing flash point outside of the laboratory. One such device is the so-called Scott Davis Portable Vapor Tester. This device uses a Wheatstone bridge circuit to determine the "Lower Explosive Limit" (LEL) of a combustible mixture of air and vapor emitted from the liquid sample. LEL represents the lower limit of flammability of a combustible vapor and is the lowest concentration of vapor in the air-vapor mixture that will propagate a flame. LEL is expressed as a percentage on a scale of 0–100%. The air-vapor mixture is drawn through an analyzing chamber, where it ignites on the surface of a resistive filament, thereby increasing the temperature within the analyzing chamber and the resistance of the filament. The increased resistance of the filament increases the voltage output of the bridge circuit. The voltage output is directly proportional to the LEL. This process typically requires one to two minutes and a human operator to draw the sample and interpret the results.

Precision Scientific Group of GCA Corporation manufactures and sells a device for measuring flash point, which is located at the site of the pipeline and automatically draws product samples therefrom. Although the device is adaptable for "in-line" use (i.e., in fluid communication with the pipeline), the device is relatively slow (i.e., approximately one to five minutes for each test cycle) and has not received widespread acceptance in the pipeline industry because of various maintenance problems, such as excessive carbon deposits in the flash chamber and the need for frequent recalibration.

There is therefore a need in the petroleum pipeline industry for a reliable device for determining the flash point of a pipeline-transported petroleum product. There is also a need in the petroleum pipeline industry for an improved "in-line" device for continually monitoring the flash point of a pipeline-transported petroleum product.

DISCLOSURE OF THE INVENTION

In accordance with the present invention, apparatus is provided for determining the flash point temperature of a liquid petroleum product being transported in a pipeline. The apparatus includes first chamber means for storing a sample of the product, product supply means communicating between the pipeline and the first chamber means for supplying the sample, air supply means for introducing air into the sample such that a mixture of air and vapor from the sample is present in the first chamber means, second chamber means communicating with the first chamber means, suction means for drawing the mixture of air and vapor from the first chamber means into the second chamber means. The second chamber means includes measuring means for measuring the Lower Explosive Limit of the mixture. Processing means is responsive to the Lower Explosive Limit for determining the flash point temperature of the sample. In one embodiment, temperature sensing means is provided for measuring the temperature of the sample and density measuring means is provided for measuring the density of the sample. The processing means is further responsive to the temperature and density of the sample for determining the flash point temperature of the sample.

In accordance with a unique feature of the invention, the measuring mean includes first and second electrically operable measuring means. The processing means is normally responsive to the Lower Explosive Limit measured by the first measuring means for determining the flash point temperature. The processing means is responsive to the Lower Explosive Limit measured by the second measuring means upon the occurrence of a predetermined condition. In one embodiment, the predetermined condition corresponds to a value of the Lower Explosive Limit measured by the first measuring means exceeding a predetermined maximum value of the Lower Explosive Limit.

In accordance with another unique feature of the invention, the first chamber means includes a bottom reservoir for storing the sample and a tube extending upwardly from the reservoir. The air-vapor mixture is drawn upwardly through the tube by the suction means. The first chamber means includes at least one baffle member located in the tube. The baffle member enhances the mixing of the air and vapor and has a plurality of apertures adapted to allow the mixture to be drawn upwardly through the tube, while substantially inhibiting liquid from being drawn upwardly through the tube. In one embodiment, the at least one baffle member includes first and second baffle members spaced apart within the tube. Each of the first and second baffle members has a substantially cylindrical shape with a substantially greater width than height. An intermediate portion of each of the first and second baffle members is recessed relative to top and bottom portions thereof such that the intermediate portion is adapted to receive a resilient member, whereby each of the first and second baffle members is adapted for sealing engagement with an inner surface of the tube.

In accordance with still another unique feature of the invention, the apparatus includes top and bottom manifold means located respectively above and below the first chamber means. The top manifold means has a generally vertical first passageway communicating with the first chamber means and first and second conduits. The first conduit communicates between the first passageway and the second chamber means, whereby the air-vapor mixture is drawn through the first conduit into the second chamber means. The apparatus further includes a purge line. The second conduit communicates between the first passageway and the purge line whereby the sample is purged from the first chamber means upwardly through the top manifold means into the purge line.

The bottom manifold means has a generally vertical second passageway communicating with the first chamber means and third and fourth conduits. The third conduit communicates between the product supply means and the second passageway, whereby the sample is supplied to the first chamber means through the bottom manifold means. The fourth conduit communicates between the air supply means and the second passageway, whereby air is supplied to the first chamber means through the bottom manifold means. The apparatus further includes a drain line communicating with the first and second passageways to allow the sample to be drained from the first chamber means downwardly through the bottom manifold means. The first and second conduits are angled downwardly to enhance drainage of the product into the first passageway and the third and fourth conduits are angled downwardly to enhance drainage of the product into the second passageway.

In operation, a sample of the product is drawn from the pipeline into the first chamber means. Air is introduced into the sample such that a combustible mixture of air and vapor from the sample is present in the first chamber means. The air-vapor mixture is suctioned from the first chamber means into the second chamber means where the vapor is ignited. The Lower Explosive Limit of the mixture is measured in the second chamber means and the flash point temperature of the sample is determined in response to the measured Lower Explosive Limit and the temperature and density of the sample.

The first chamber means is purged of a previous sample and the second chamber means is purged of vapor from the previous sample prior to drawing the sample into the first chamber means. Purging preferably includes flushing product through the first chamber means and drawing air through the second chamber means for a predetermined time period. After purging and before drawing the sample into the first chamber means, the first chamber means is drained to remove the purging product.

After the sample has been tested to determine its flash point temperature, the sample is purged from the first chamber means. If the flash point temperature of the sample is determined to be outside a predetermined range of acceptable flash point temperatures, an alarm signal (which may include an audible and/or visual alarm) is generated to alert the operator.

Figure 1:
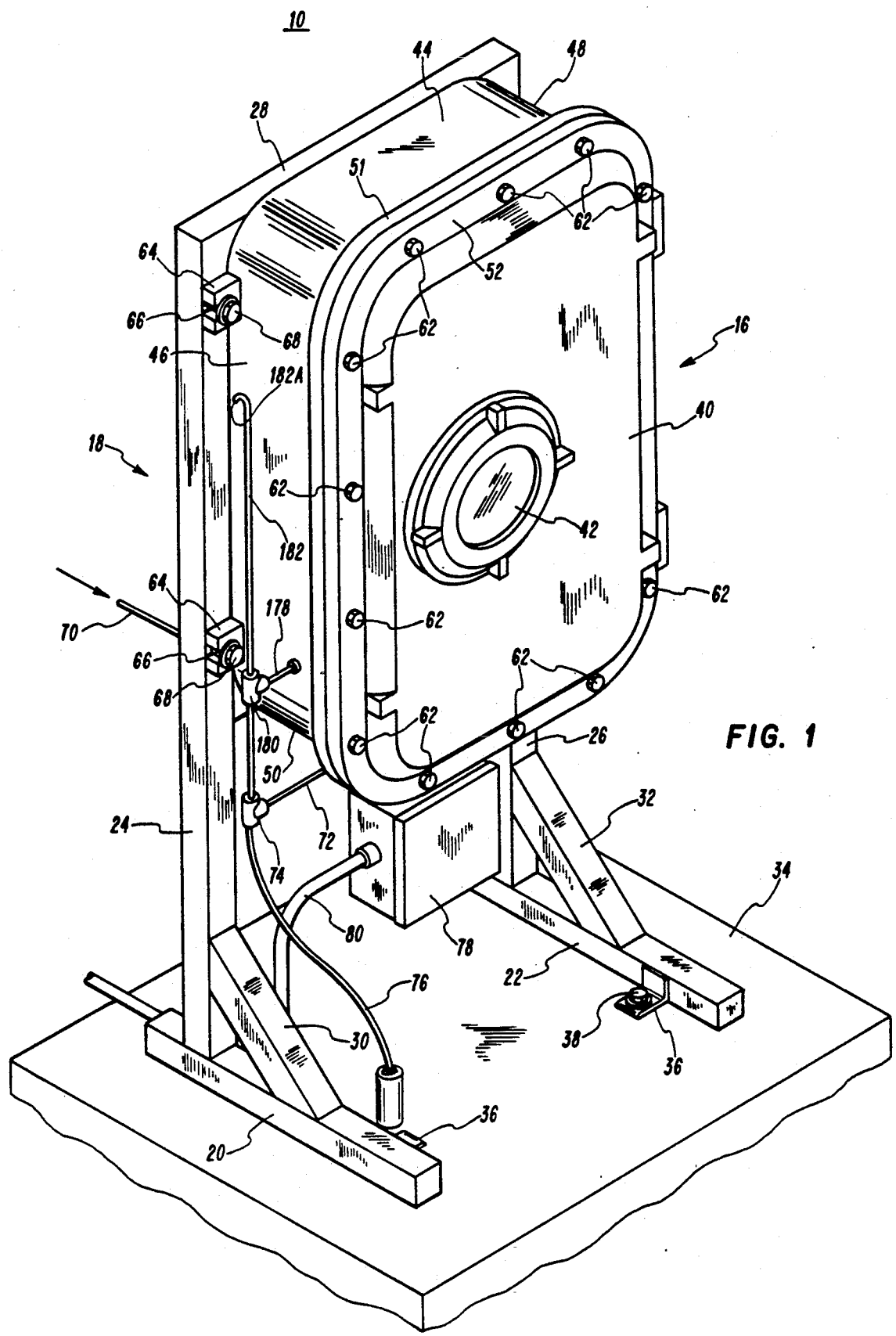
FIG. 1 is a perspective view of an apparatus for monitoring the flash point of a pipeline-transported petroleum product, according to the present invention.

FIG.'s 10-14 are respective flow diagrams, illustrating the sequence of operation of the apparatus of FIG. 1.

DETAILED DESCRIPTION OF THE PREFERRED EMBODIMENT

In the description which follows, like parts are marked throughout the specification and drawings with the same respective reference numerals. The drawings are not necessarily to scale and in some instances proportions may have been exaggerated in order to more clearly depict certain features of the invention.

In accordance with the present invention, apparatus is provided for determining the flash point of a pipeline-transported petroleum product. The apparatus is preferably located adjacent the pipeline and is in fluid communication therewith to provide an "in-line" system for continually and automatically monitoring the flash point of the product with minimal operator intervention.

Referring now to FIG.'s 1 and 2, apparatus 10 is provided for continually and automatically monitoring the flash point of a liquid petroleum product 12 flowing through a petroleum pipeline 14. Apparatus 10 includes a substantially rectangular housing 16, which is mounted in an upright position on a support frame 18. Support frame 18 includes first and second base support legs 20 and 22, respectively, and first and second upstanding support beams 24 and 26, respectively, depending upwardly from the respective first and second support legs 20 and 22. A generally horizontal cross-beam 28 extends between first and second upstanding beams 24 and 26 to define a top portion of frame 18. First and second support braces 30 and 32 extend between first base support leg 20 and first upstanding beam 24 and between second support leg 22 and second upstanding beam 26, respectively. First and second base support legs 20 and 22 are anchored to a base support surface 34, such as a concrete pad, by means of respective elbow brackets 36 and mounting bolts 38.

Housing 16 includes a hinged door panel 40 having a circular window 42 to permit at least a portion of the interior of housing 16 to be viewed from outside housing 16. The remainder of housing 16 is comprised of a top panel 44, opposed side panels 46 and 48, and a bottom panel 50, which are integrally formed.

Referring also to FIG.'s 3 and 4, housing 16 includes first and second flanges 51 and 52. First flange 51 has a relatively flat surface 54 and a plurality of apertures 56. Second flange 52 has a relatively flat surface 58 and a plurality of apertures 60. Second flange 52 is located on door panel 40. When door panel 40 is in a closed position, as shown in FIG. 1, apertures 60 are aligned with respective apertures 56 for receiving respective mounting bolts 62, whereby door panel 40 is secured in a closed position, with flange surfaces 54 and 58 in facing contact. Housing 16 further includes four mounting brackets 64 (two of which are shown in FIG.'s 1 and 2) adjacent the respective four corners of housing 16. Each mounting bracket 64 has an elongated slot 66 to accommodate a mounting bolt 68, whereby housing 16 is secured to the respective beams 24 and 26.

A sample of the petroleum product 12 is taken from pipeline 14 and introduced into housing 16 through a one-quarter inch stainless steel product supply line 70. After the sample has been tested, it is expelled from housing 16 through a one-half inch stainless steel drain line 72. Drain line 72 is connected by a T-fitting 74 to an external drain line 76.

Apparatus 10 further includes an electrical junction box 78 through which the external electrical connections to apparatus 10 are made. A multi-conductor electrical cable 80 is coupled to junction box 78. The electrical connections include a 120 volt AC power input and an electrical input from gravitometer transducer 82, which provides an input signal indicating the density of the product sample. The density is preferably indicated in American Petroleum Institute (API) gravity units.

Figure 2:
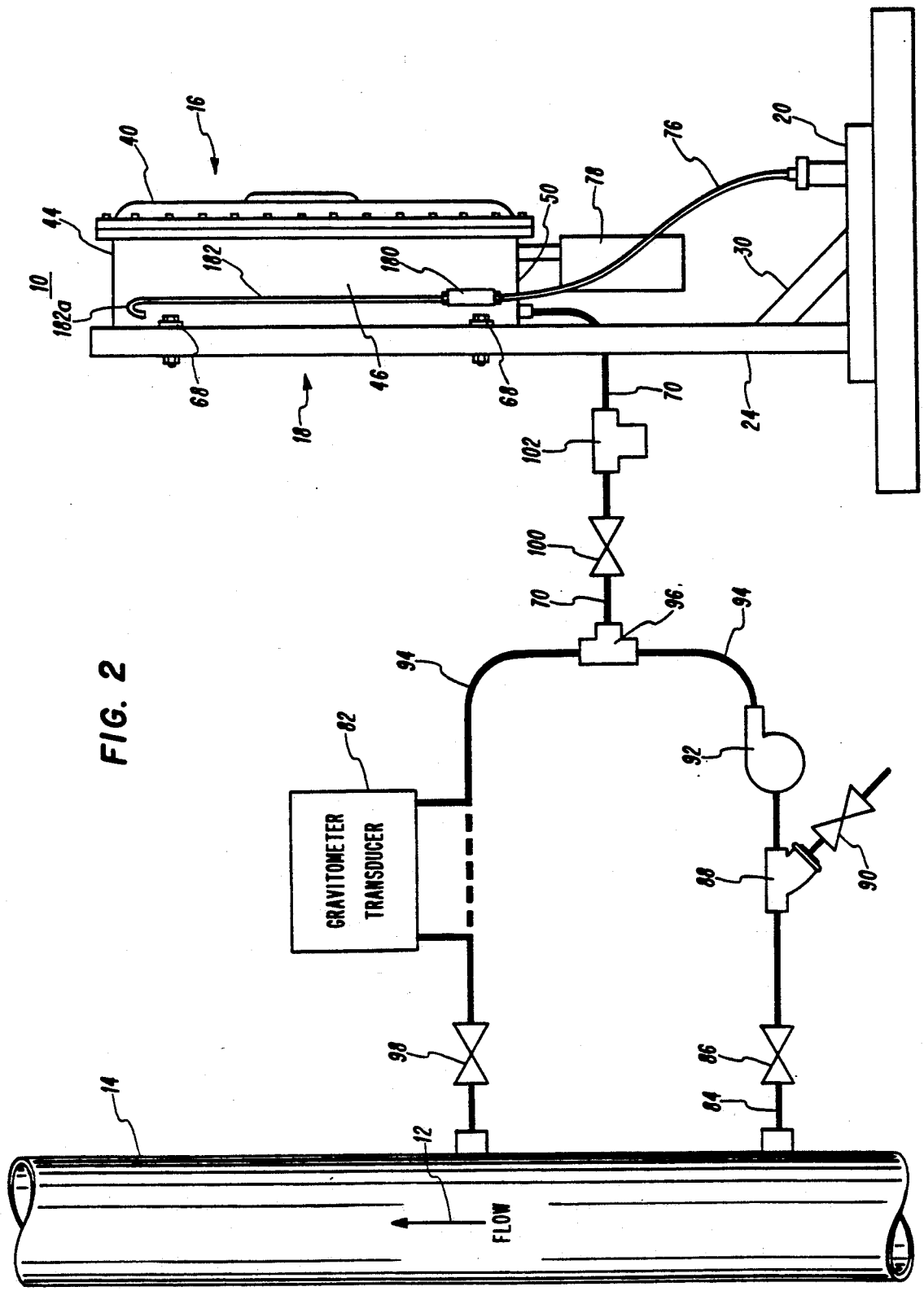
FIG. 2 is a schematic illustrating the "in-line" operation of the apparatus of FIG.1.

Referring now to FIG. 2, apparatus 10 is in fluid communication with pipeline 14. Product 12 is drawn from pipeline 14 through suction line 84 by pump 92. Suction line 84 includes a valve 86, for controlling the flow through suction line 84, a "Y" type strainer 88 for filtering particulate matter and a ball valve 90, which is open when strainer 88 is flushed out. Pump 92 discharges the product through discharge line 94 to T-fitting 96. Some of the product flows into supply line 70, while the remainder returns to pipeline 14 through discharge line 94. The API gravity of the product is measured by gravitometer transducer 82. A valve 98 is located in discharge line 94 for controlling the return flow to pipeline 14. A valve 100 and filter 102 are located in supply line 70. Valve 100 controls the flow of product into housing 16. Filter 102 is preferably a 140 micron "T" type filter for filtering out particulates.

Referring now to FIG.'s 3 and 4, the product sample enters housing 16 through supply line 70. A solenoid-operated inlet isolation valve 104 is normally in an open position for allowing the product to flow through supply line 70. Valve 104 is normally open, but is closed in response to a loss of power condition or in response to an electrical signal from float valve 106, which indicates that housing 16 is flooded. Flooding may result from leakage of product into housing 16.

A pressure regulator 108 controls the pressure in supply line 70, to maintain the line pressure between pressure regulator 108 and a product inlet valve 110 at approximately 25 psi. A pressure relief valve 109 relieves excess pressure in line 70 on the discharge side of regulator 108. Typically, valve 109 is set to open at 100 psi. When valve 109 is open, product is discharged through line 111 into a purge line 166. Inlet valve 110 is a solenoid-operated valve, which is selectively opened and closed to control the flow of product entering a sample chamber 112. A solenoid-operated drain valve 114 is normally closed, except when product is being drained from chamber 112 through drain line 72.

Figure 7:
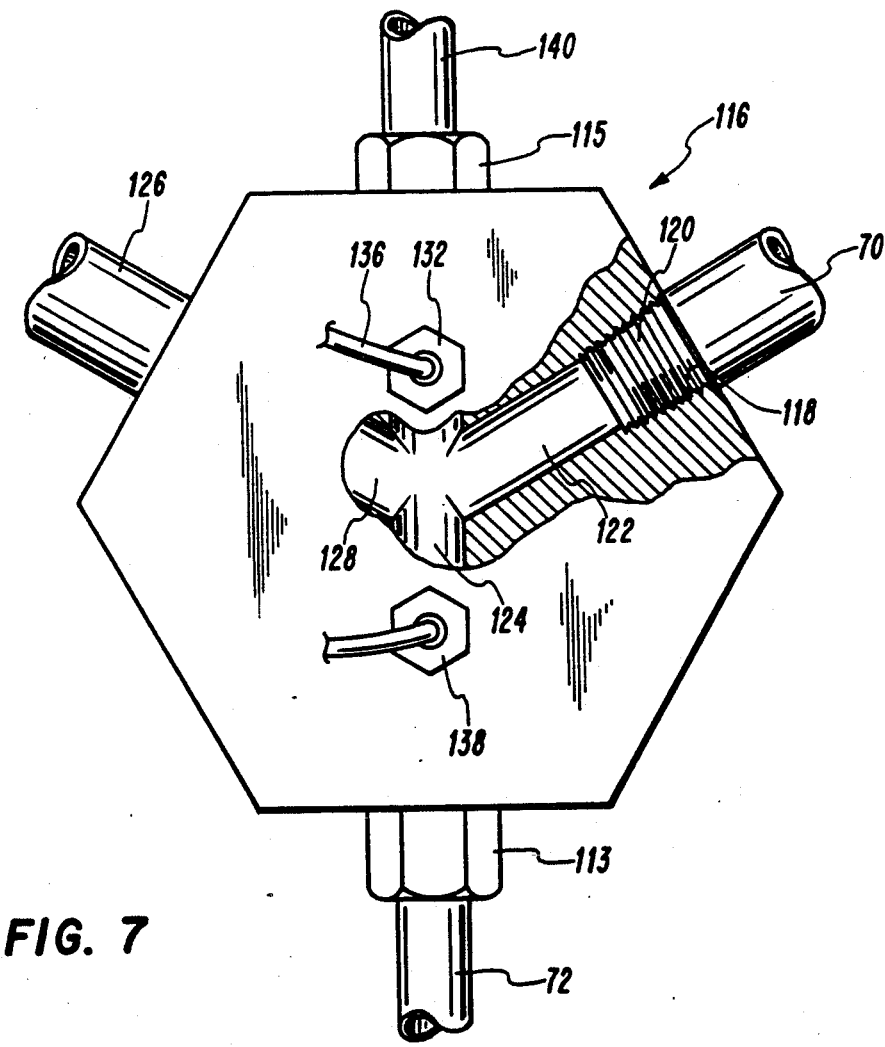
FIG. 7 is an elevation view of a manifold component in which air is introduced into the product sample, with a portion of the manifold block broken away to show the interior thereof.

Referring also to FIG. 7, the incoming product flows through inlet valve 110 into a hexagonal bottom manifold 116. Bottom manifold 116 includes a threaded port 118 for receiving a complementary threaded male fitting 120 on the discharge end of inlet line 70. Port 118 is angled downwardly at an angle of approximately 45° and communicates with a downwardly angled conduit 122. Conduit 122 communicates between port 118 and a generally vertical passageway 124.

Bottom manifold 116 includes another threaded port (not shown) on an opposite side of manifold 116 for receiving a complementary threaded male fitting (not shown) on the discharge end of an air supply line 126. The threaded port connected to air supply line 126 is also angled downwardly at an angle of approximately 45° and communicates with a downwardly angled conduit 128, which branches into passageway 124. A solenoid-operated valve 130 controls the flow of air into manifold 116. When drain valve 114 and air supply valve 130 are closed, the incoming product flows upwardly through passageway 124 into a reservoir 112a of sample chamber 112. Air introduced into manifold 116 through air supply line 126 mixes with the liquid product in reservoir 112a so that a mixture of air and flammable vapor from the product is bubbled upwardly into chamber 112 when suction pressure is applied to chamber 112. The downwardly angled conduits 122 and 128 facilitate drainage when the product is drained from sample chamber 112, as will be described in greater detail hereinafter.

An optical sensor 132 is located in passageway 124 for detecting the presence of liquid therein. Sensor 132 is coupled to an optical sensor control module 134 by a fiber optic cable 36. Module 134 generates an electrical signal when liquid is present at or above the position of sensor 132. When the liquid level drops below the position of sensor 132, the electrical signal is not generated.

Control module 134 is preferably a optical sensor control module of the SM 312 F type, manufactured and sold by Banner Engineering.

A temperature sensor 138 is also located in passageway 124 for measuring the temperature of the liquid therein. The temperature of the product is one of the factors used to determine the flash point of the product sample, as will be described in greater detail hereinafter.

Liquid flows upwardly through passageway 124 and fill line 140 into reservoir 112a. Although not shown in FIG. 7, manifold 116 includes top and bottom generally vertical threaded ports for matingly engaging complementary threaded male fittings (not shown) on the respective ends on drain line 72 and fill line 140, for connecting the respective lines 72 and 140 to passageway 124 at the respective bottom and top ends thereof. Attachment nuts 113 and 115 secure the respective lines 72 and 140 to manifold 116.

Figure 9:
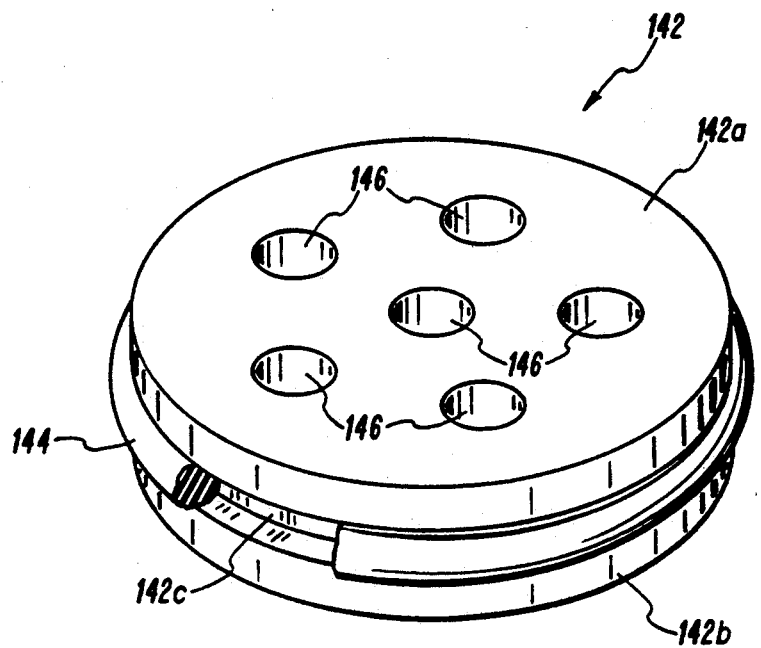
FIG. 9 is a perspective view of a baffle member, which is located in a product sample chamber, to enhance the separation of vapor from the liquid sample.

Sample chamber 112 is filled to a level at approximately the top end 112b of reservoir 112a, which is coincident with the bottom of a cylindrical glass tube 112c. Tube 112c defines an intermediate portion of sample chamber 112. A pair of cylindrical baffles 142, which are preferably comprised of teflon material, are located in tube 112c. Each baffle is relatively flat, with a substantially greater width than height. Referring also to FIG. 9, each baffle 142 is comprised of top and bottom portions 142a and 142b and a recessed intermediate portion 142c for receiving a resilient member, such as an O-ring 144. O-ring 144 engages an inner surface of tube 112c to locate the corresponding baffle 142 in sealing engagement within tube 112c. Each baffle 142 further includes a plurality of apertures 146, communicating between top and bottom portions 142a and 142b. The air-vapor mixture is drawn upwardly through tube 112c by a vacuum pump 148. Vacuum pump 148 also exerts suction pressure on chamber 112 to draw air into manifold 116 from line 126. Baffles 142 enhance the mixing of the air and vapor and substantially inhibit the passage of liquid through tube 112c, but allow the air-vapor mixture to pass through the respective apertures 146.

An hexagonal top manifold 150 is located above tube 112c. Manifold 150 has substantially the same configuration as manifold 116. Manifold 150 has downwardly angled threaded ports on respective opposite sides of manifold 150. The threaded ports are in fluid communication with respective downwardly angled conduits in the interior of manifold 150. Each of the conduits communicates with a generally vertical passageway. Manifold 150 further includes top and bottom threaded ports in communication with the passageway. The top and bottom threaded ports are adapted to matingly engage respective complementary threaded members on the ends of respective lines 152 and 154. Line 152 functions as an air inlet line for admitting air into the passageway of manifold 150 during a "drain" cycle when product is being drained from sample chamber 112. The drain cycle will be described in greater detail hereinafter. Line 154 communicates between tube 112c and manifold 150. An air filter 156 is located in air inlet line 152 to filter dirt and other contaminants from the air entering manifold 150. Air inlet line 152 is connected by means of a T-fitting 158 to an air supply line 160, which is connected to an inlet end of an air flow meter 161. Meter 161 measures the rate of air flow. Air supply line 126 is connected to the outlet end of meter 161 for supplying air to bottom manifold 116.

One of the angled ports of top manifold 150 is adapted to matingly engage a complementary threaded male fitting on the end of an outlet line 162 through which air-vapor mixture from the product sample flows into a sensing chamber block 164. The other angled port is adapted to matingly engage a complementary threaded male fitting on the end of an outlet line 166 through which the sample is purged from sample chamber 112 during a "purge" cycle, which will be described in greater detail hereinafter. Line 166 is connected to drain line 72 by T-fitting 167 below drain valve 114 so that the liquid product can be purged from sample chamber 112 when drain valve 114 is closed.

An optical sensor 168 is located in the central passageway of top manifold 150 to detect the presence of liquid within the passageway of top manifold 150. A fiber optic cable 170 connects sensor 168 to a control module 172, which generates an electrical signal in response to the liquid being detected by sensor 168 in the passageway of top manifold 150. Control module 172 is preferably an optical sensor control module of the SM 312 F type, manufactured and sold by Banner Engineering.

Pump 148 is an electrical pump, which operates on 120 volt AC power. The speed of pump 148 is controlled by a dimmer control switch 174. In operation, pump 148 draws air into manifold 116 to aerate the liquid sample and draws the air-vapor mixture upwardly through tube 112c and top manifold 150 and through discharge line 162 into chamber block 164. The flash point of the sample is determined by measuring the LEL of the airvapor mixture in chamber block 164. While the vapor is being tested, pump 148 sucks the vapor from chamber block 164 through a vapor suction line 176 and discharges the vapor through a vapor discharge line 178 to the outside of housing 16.

As can be best seen in FIG. 1, vapor discharge line 178 is coupled by means of a T-fitting 180 to a vent line 182, which is open to the atmosphere at a top end 182a thereof. The airvapor mixture is discharged to the atmosphere through vent line 182. A 40 micron filter 184 is located in suction line 176 to prevent dirt and other solid material from being sucked into vacuum pump 148.

A needle valve 186 is located in supply line 126 for regulating the volume of air supplied to lower manifold 116. A second air supply line 188 is attached by means of a T-fitting 190 to air supply line 126. A solenoid-operated three-way valve 192 closes supply line 188, to allow the air-vapor mixture to flow into chamber 164 through lines 162 and 194. When it is desired to purge the air-vapor mixture from block 164, valve 192 closes line 162, to isolate block 164 from manifold 150, and opens line 188 to allow fresh air to flow through inlet line 194 and block 164, to purge block 164 after each sampling cycle. A needle valve 196 is located in line 188 to regulate the volume of air flowing through line 188.

A solenoid-activated valve 198 controls the flow of air into top manifold 150. Another solenoid-operated valve 200 controls the flow of liquid product through purge line 166.

Figure 8:
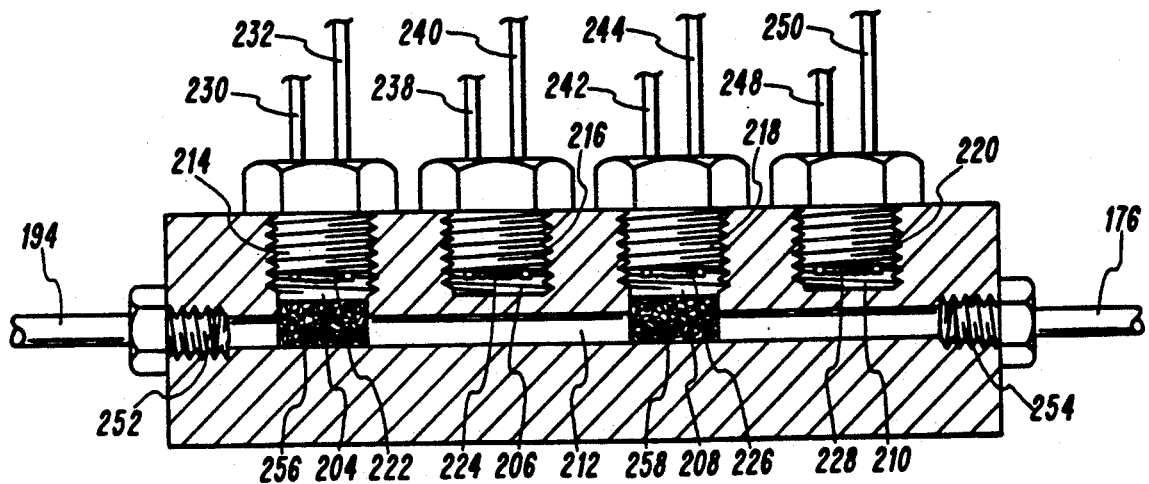
FIG. 8 is a sectional view of a testing chamber for measuring the LEL of a mixture of air and vapor from the product sample.

Referring also to FIG. 8, block 164 has four internal chambers 204, 206, 208 and 210 and a central bore 212 extending longitudinally through block 164. Chambers 204 and 208 communicate with bore 212. Chambers 206 and 210 are sealed. Respective internal surfaces of block 164 defining the respective chambers 204, 206, 208 and 210 are at least partially threaded for engaging respective complementary threaded male fittings 214, 216, 218 and 220. Electrically resistive filaments 222, 224, 226 and 228 are mounted on the respective ends of threaded fittings 214, 216, 218 and 220. Filaments 222, 224, 226 and 228 are preferably comprised of platinum material.

Figure 5:
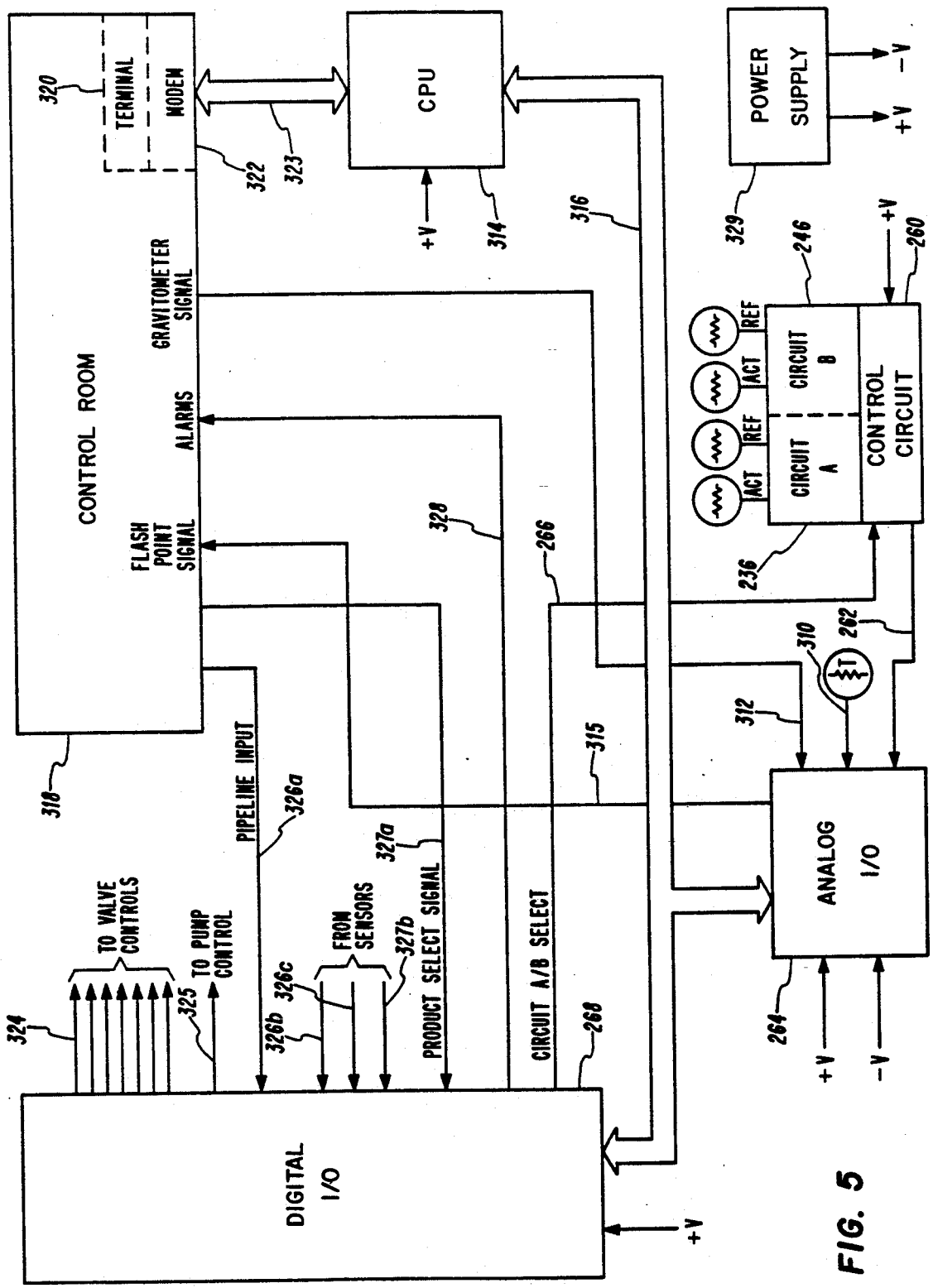
FIG. 5 is a schematic illustrating the electronic control system of the apparatus of FIG. 1.

Referring also FIG. 5, filament 222 is electrically coupled by conductors 230 and 232 to a first circuit 236 (Circuit A). Filament 224 is also coupled to first circuit 236 by conductors 238 and 240. First circuit 236, including filaments 222 and 224, defines a first Wheatstone bridge circuit.

Filament 226 is coupled by conductors 242 and 244 to a second circuit 246 (Circuit B). Filament 228 is also coupled to second circuit 246 by conductors 248 and 250. Second circuit 246, including filaments 226 and 228, defines a second Wheatstone bridge circuit.

Line 194 has a threaded male fitting 252, which engages complementary female threads adjacent an inlet end of bore 212, for coupling inlet line 194 to block 164. Similarly, outlet line 176 has a threaded male fitting 254, which is adapted to engage complementary female threads at the opposite end of bore 212, for coupling outlet line 176 to block 164. The air-vapor mixture is drawn through line 194 into bore 212. Filaments 222, 224, 226 and 228 are heated by electrical current so that when a combustible air-vapor mixture is present in bore 212, the vapor will ignite, thereby increasing the temperature and electrical resistance of filaments 222 and 226.

In the absence of the combustible mixture, the electrical resistances of filaments of 222, 224, 226 and 228 are approximately equal (e.g., approximately 0.6 ohm). However, when the vapor ignites, the temperature and electrical resistance of filaments 222 and 226 are increased, which results in an unbalanced condition in the corresponding Wheatstone bridge circuits. Filaments 222 and 226 are therefore "active" filaments, while 224 and 228 are "reference" filaments. Flame arresters 256 and 258 are located in respective chambers 204 and 206 to inhibit flaming within chambers 204 and 208. Flame arresters 256 and 258 are preferably comprised of a wire mesh material.

In accordance with a unique feature of the invention, two separate flash point testing circuits are provided. First circuit 236, which includes active filament 222 and reference filament 224, operates independently of second circuit 246, which includes active filament 226 and reference filament 228. In normal operation, first circuit 236 is used to determine the flash point of a product sample, but second circuit 246 is available as a backup circuit in the event of a malfunction or other condition which prevents first circuit 236 from accurately determining the LEL of the mixture. The testing circuit is automatically switched from first circuit 236 to second 246 in response to a selected condition, as will be described in greater detail hereinafter.

A control circuit 260 transmits an analog signal 262 to an analog input/output (I/O) mounting rack 264. Control circuit 260 is responsive to an input signal 266 from a digital I/O mounting rack 268 for activating a selected one of the flash point testing circuits (i.e., either Circuit A or Circuit B). Analog I/O 264 is preferably an analog I/O mounting rack of the PB4AH type, manufactured and sold by Opto 22. Digital I/O 268 is preferably a digital I/O mounting rack of the G4PB16H type, manufactured and sold by Opto 22. The operation of digital I/O 268 is controlled by a brain board 270, which is preferably of the B1 type, manufactured and sold by Opto 22. The operation of analog I/O 264 is controlled by a brain board 272, which is preferably a brain board of the B2 type, manufactured and sold by Opto 22. First and second circuits 236 and 246 and control circuit 260 are preferably mounted on a printed circuit board 274.

Figure 3:
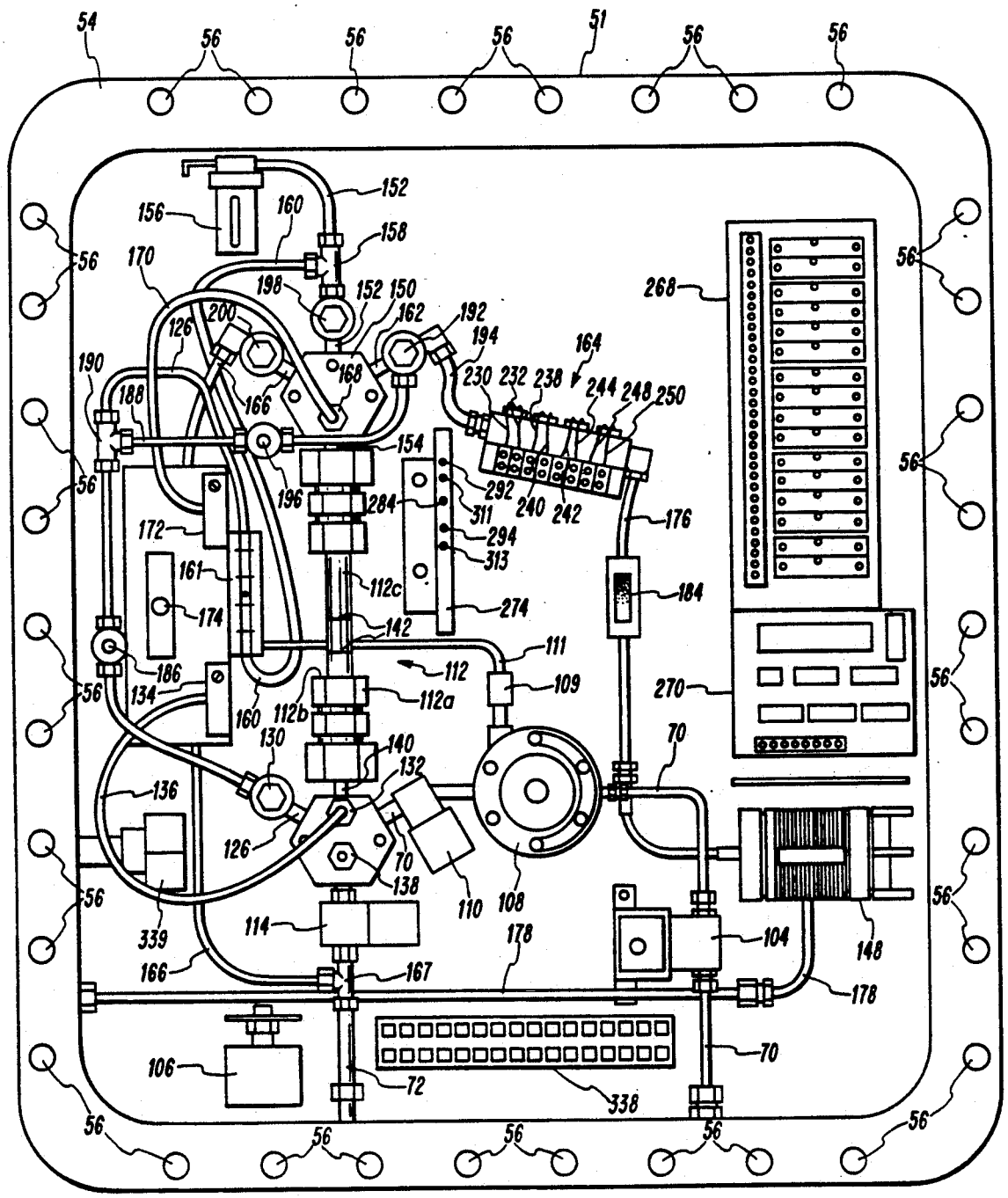
FIG. 3 is an elevation view of the interior of the apparatus housing, looking toward a back panel of the housing.
Figure 4:
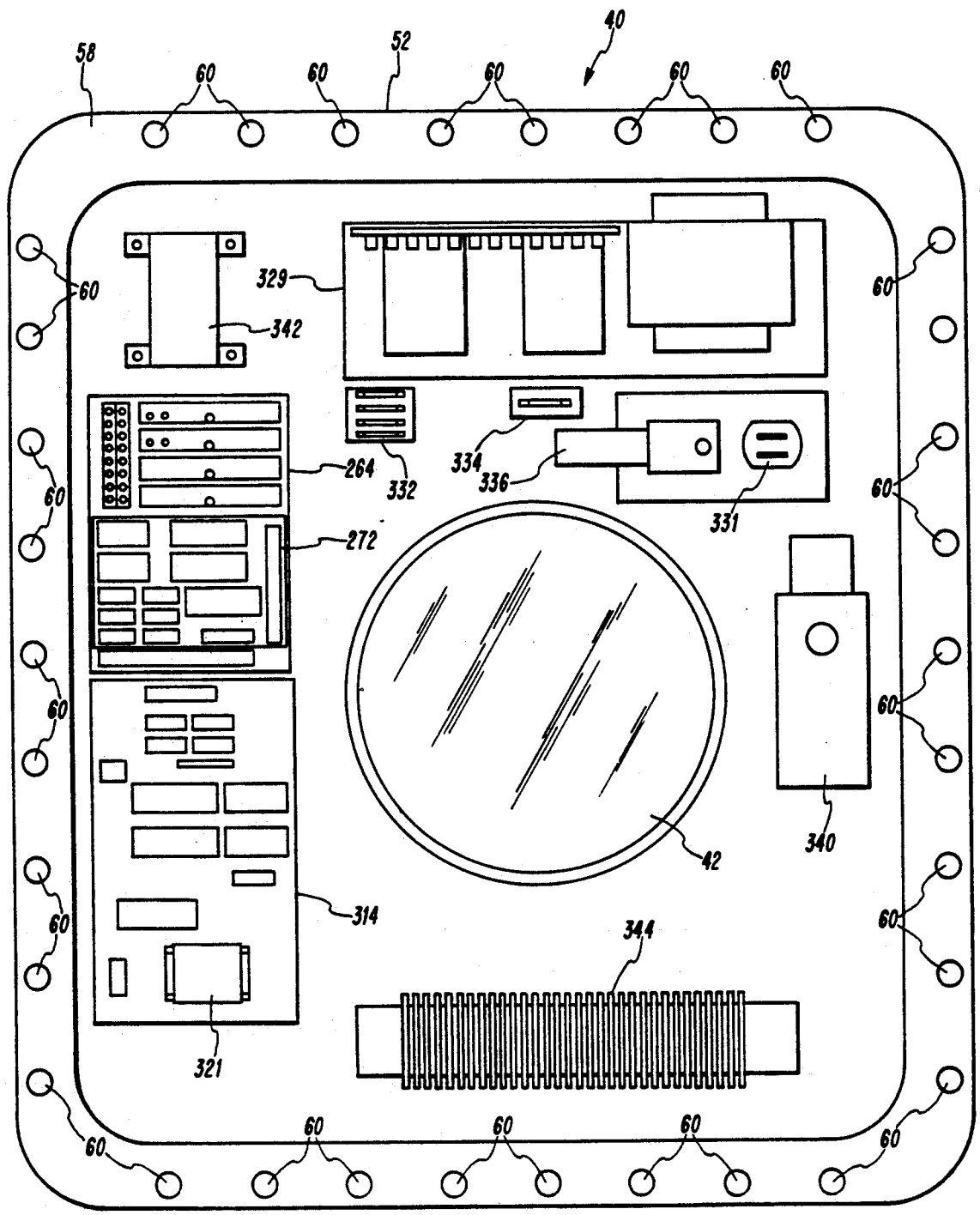
FIG. 4 is an elevation view of the interior of the apparatus housing, looking toward a front panel of the housing.
Figure 6:
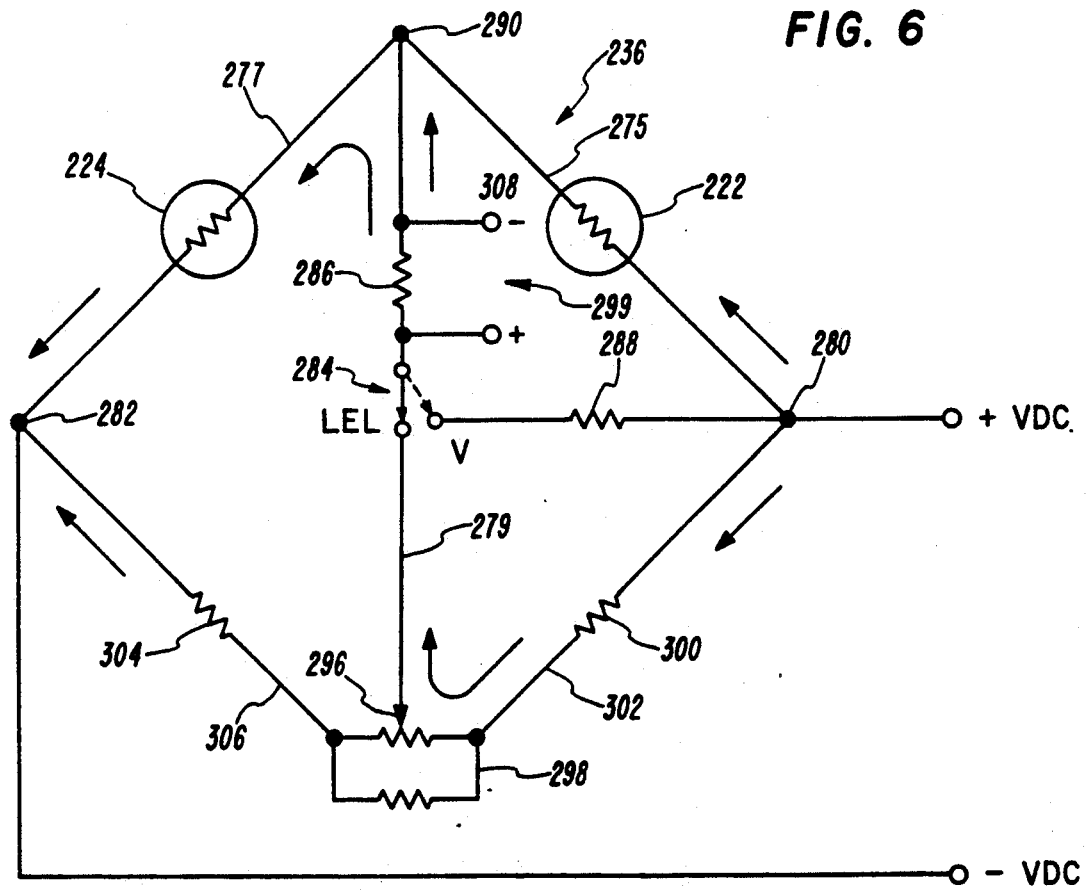
FIG. 6 is an electrical circuit diagram of a Wheatstone bridge circuit used in determining the flash point of a sample of the petroleum product.

The operation of first bridge circuit 236 will now be described with reference to FIG. 6. One skilled in the art will appreciate that the operation of second bridge circuit 246 is substantially the same as first circuit 236. FIG. 6 illustrates a Wheatstone bridge circuit in which filaments 222 and 224 define respective legs 275 and 277 of the bridge circuit. An input voltage +VDC is applied to node 280 of bridge circuit 236. The opposite node 282 is grounded (−VDC). A two position switch 284 is moveable between a first position indicated by the dashed lines and a second position indicated by the solid line. The input voltage is adjusted to achieve an output voltage across resistor 286 of 25 millivolts (mv) in a center leg 279 of the bridge circuit, which represents a mid-level voltage between a 0–50 mv output voltage range. When switch 284 is in the position indicated by the dashed lines, electrical current flows through resistor 288 and resistor 286. Resistor 286 has an electrical resistance of approximately 24.9 ohms and resistor 288 has an electrical resistance of approximately 1000 ohms. The input voltage is adjusted so that there is approximately a 1.025 voltage drop across active filament 222 between node 280 and node 290. The input voltage is adjusted by means of a user operable adjustment screw 292 (see FIG. 3). A second voltage adjustment screw 294 is provided for adjusting the voltage output of second bridge circuit 246 in the same manner as described above.

When the input voltage has been adjusted to achieve the desired 25 mv output voltage, switch 284 is moved to the second position, as shown by the solid line in FIG. 6. Bridge circuit 236 is balanced when the voltage at node 296 is the same as the voltage at node 290 such that no electrical current flows through center leg 279. As previously indicated, the electrical resistances of active filament 222 and reference filament 224 are substantially the same. However, bridge circuit 236 must be balanced for differences in the electrical resistance between filaments 222 and 224, which may occur as a result of deterioration of active filament 222.

Bridge circuit 236 is balanced by positioning node 296 with respect to a resistor circuit 298 so that the voltage at node 296 is substantially the same as the voltage at node 290. In this condition, no current flows through center leg 279. Resistor circuit 298 is comprised of two 10 ohm resistors in parallel, which provide a 5 ohm resistance in series. Bridge circuit 236 further includes a 20 ohm resistor 300 between node 280 and node 296, which defines a leg 302 of bridge circuit 236 and a 20 ohm resistor 304 between node 296 and node 282, which defines a leg 306 of bridge circuit 236. Node 296 may be adjusted to provide a small "zero offset" voltage (e.g., 5 mv) so that the voltage output of bridge circuit 236 is measured relative to the zero output voltage. User operable adjustment screws 311 and 313 (FIG. 3) are provided to allow the operator to adjust the respective zero offset voltages of first and second circuits 236 and 246.

As previously indicated, the electrical resistance of active filament 222 increases when the air-vapor mixture ignites on the surface of filament 222. The electrical resistance of filament 222 increases in direct proportion to the LEL of the sample vapor. The increased resistance of filament 222 results in an increased voltage drop across filament 222 (i.e., between node 280 and node 290), which decreases the voltage at node 290, thereby resulting in an electrical current through center leg 279 in the direction of arrow 308. The amplitude of the current is in direct proportion to the voltage differential between node 290 and node 296. The current flowing through center leg 279 produces a voltage output 299 across resistor 286 in direct proportion to the amplitude of the current. Voltage output 299 indicates the LEL of the vapor sample and is transmitted by control circuit 260 as output signal 262 to analog I/O 264 (see FIG. 5). Temperature sensor 138 transmits an analog signal 310 to analog I/O 264, indicating the temperature of the liquid sample. A third analog signal 312 is transmitted to analog I/O mounting rack 264 by gravitometer 82, which represents the API gravity of the sample.

Apparatus 10 further includes a central processing unit 314, which includes a microprocessor. The microprocessor is preferably a microprocessor of the Z-80 type. CPU 314 controls the operation of apparatus 10. CPU 314 communicates with digital I/O 268 and analog I/O 264 by means of a RS485 interface 316. CPU 314 is responsive to data representing the LEL, temperature and API gravity of the sample for computing the flash point temperature of the sample. The flash point temperature is transmitted as an analog signal 315 in the 4-20 milliamp (ma) range by analog I/O 264 to a control room 318, which is preferably located at a remote location from apparatus 10. CPU 314 communicates with a handheld terminal 320, which is preferably located at a remote location from apparatus 10 for displaying selected parameters, including the flash point temperature of the sample. CPU 314 is also configured to interface with a modem 322 for transmitting data by telecommunications link. A RS485/RS232 converter 321 is provided for data transmission between CPU 314 and terminal 320 and modem 322 via a RS 232 interface 323.

Digital I/O 268 is responsive to control signals from CPU 314 for outputting respective control signals 324 for controlling the various solenoid operated valves 104, 110, 114, 130, 192, 198 and 200. Digital I/O 268 also generates a control signal 325 for controlling vacuum pump 148. Digital I/O 268 receives a digital input signal 326a indicating the flow status of pipeline 14 (i.e., whether there is a flow in pipeline 14). Input signals 326b and 326c are received from the high and low level optical sensors 172 and 134, respectively. A product select signal 327a indicates the type of product flowing in pipeline 14. Digital I/O 268 also receives an input signal 327b from float sensor 106, which monitors leakage in housing 16. Digital I/O 268 also generates various alarm signals 328 in response to selected conditions. For example, an alarm signal is generated when the flash point of the sample falls outside of acceptable limits for a particular type of product and in the event of a sensor component malfunction. As previously indicated, digital I/O 268 generates an output signal 266 in response to a control signal from CPU 314 for switching the active sensing circuit from first circuit 236 to second circuit 246 in the event of a malfunction of first circuit 236.

Referring to FIG.'s 4 and 5, a power supply 329 is mounted on the inside of door panel 40. Power supply 329 provides a source of DC electrical power at +24, +5, +15 and -15 volts DC. 120 volt AC electrical power is supplied for the solenoid operated valves 104, 110, 114, 130, 192, 198 and 200 and for vacuum pump 148. An electrical plug-in socket 331 is provided for an electrical service connection. All of the control components of apparatus 10, including CPU 314, digital I/O 268 and analog I/O 264, operate on DC electrical power. CPU 314 operates on +5 volt DC power. RS485/RS232 converter 321 operates on +15 volt DC power. Control circuit 260 and bridge circuits 236 and 246 operate on +24 volt DC power. Digital I/O 268 operates on +5 volt and +24 volt DC power and 120 volt AC power. Analog I/O 264 operates on +24, +5, +15 and -15 volt DC power. A DC power supply fuse box 332 is provided for the four separate DC voltages An AC power supply fuse box 334 is provided for the 120 volt AC. A lamp 336 is provided for illuminating the interior of housing 16. A terminal block 338 is provided for various AC and DC power connections. An electrical power switch 339 is also located in housing 16 for selectively connecting electrical power to and disconnecting electrical power from apparatus 10.

A thermostat 340 is located on the inside of door panel 40 for maintaining a predetermined temperature within housing 16. A fan 342 is provided for cooling the interior of housing 16 and a heater 344, which operates on 120 volt AC power, is provided for heating the interior of housing 16.

Figure 10:
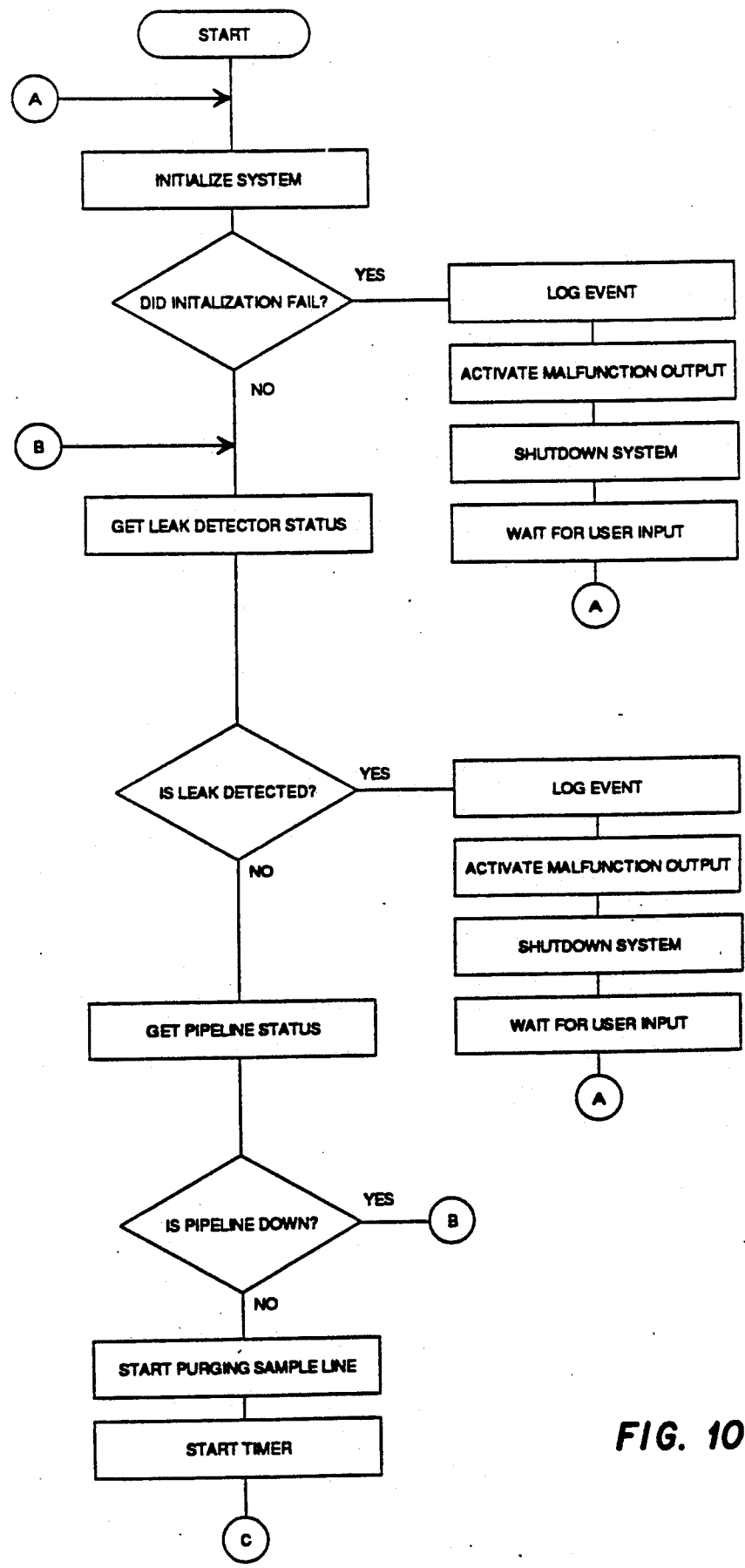
Figure 11:
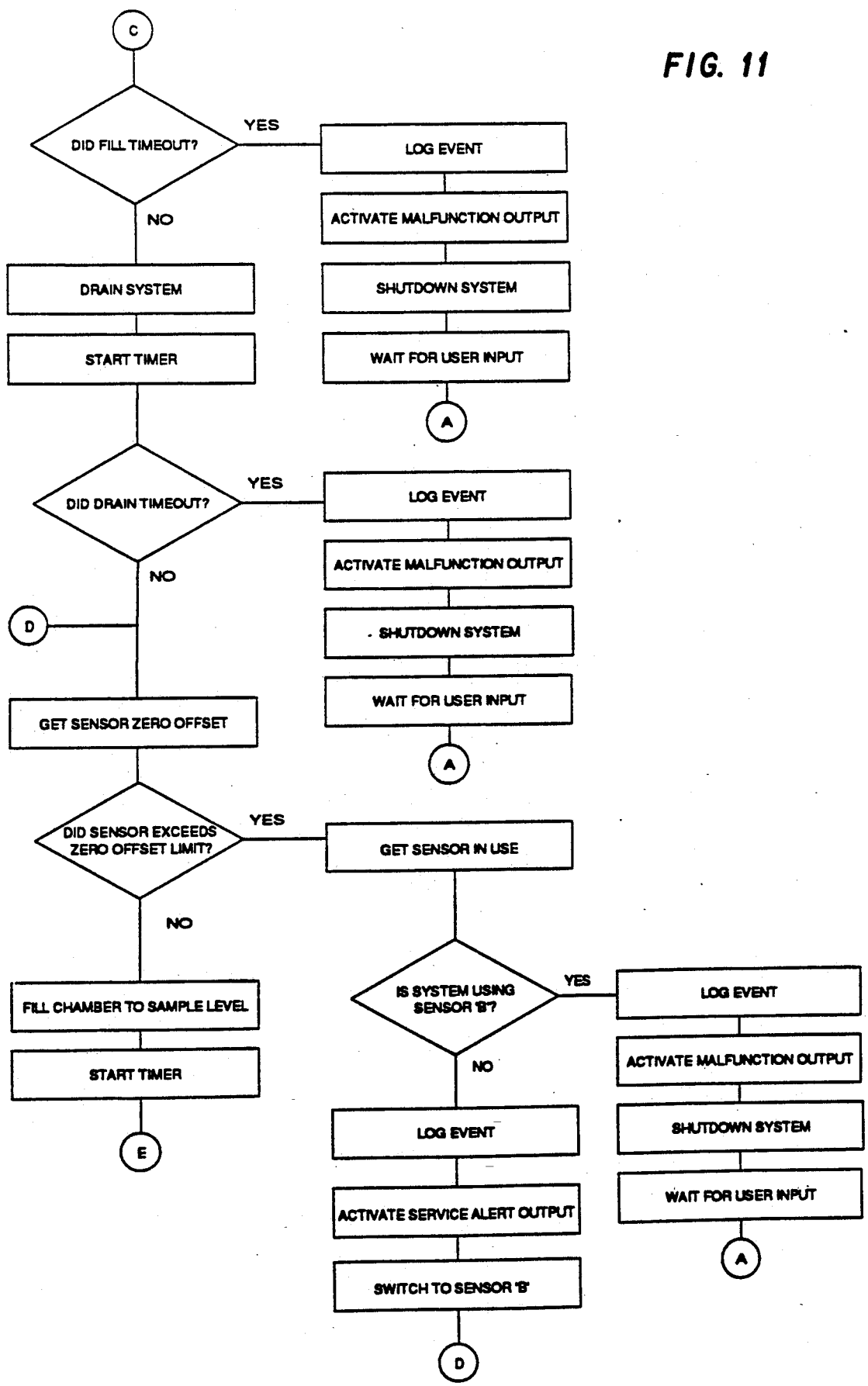
Figure 12:
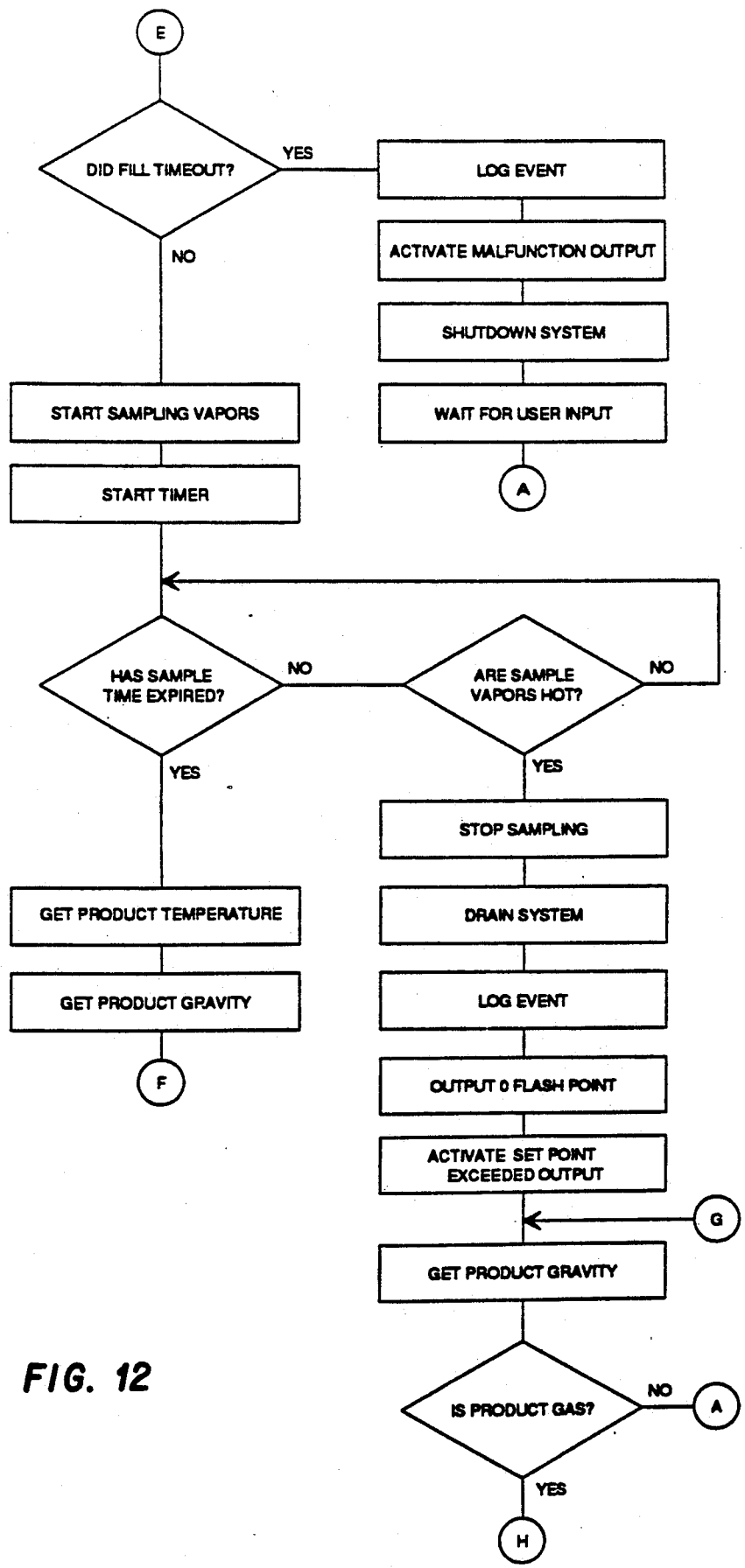

Referring also to FIG.'s 10-14, the operation of apparatus 10 will now be described in detail. CPU 314 automatically controls the operation of apparatus 10 in accordance with a programmed set of control instructions. As shown in FIG. 10, upon initialization of operation, CPU 314 will check the status of float valve 106 to determine whether leakage has been detected within housing 16. If for any reason initialization fails, the event is stored in the system memory and digital I/O 68 generates a malfunctional alarm, which interrupts the operation of the system until it is re-started by an input command entered by the operator via hand-held terminal 320.

If initialization is accomplished and no leak is detected in housing 16, the system determines the status of pipeline 14 to determine whether product is flowing within pipeline 14. If no product is flowing within pipeline 14, the system will continue to monitor float valve 106 to check for leakage and to monitor the status of pipeline 14 until a flow of product is detected within pipeline 14, which is indicated by input signal 326a to digital I/O 268.

When a flow is detected in pipeline 14, the system will begin the "purge" cycle to flush out product supply lines 84 and 70 and sample chamber 112. The purge cycle will typically last approximately five seconds. During the purge cycle valves 104 and 110 are open and valves 114 and 130 are closed so that product flows into housing 16 through supply line 70 and upwardly through sample chamber 112. Valve 198 is closed and valve 192 closes line 162, but allows air from line 188 to be sucked through line 194 into block 164 to purge the vapor from the previous sample from block 164. Valve 200 is open so that the liquid product flows through purge line 166 into drain line 72.

During the purge cycle, high level sensor 172 should detect the presence of liquid within top manifold 150. If top level sensor 172 does not generate an electrical signal indicating the presence of liquid in top manifold 150 during a period of time corresponding to two purge cycles (e.g., 10 seconds), a blockage in one or both of the product supply lines 70 and 84 or in the sample chamber 112 is indicated, whereupon the system will log the event, activate a malfunction alarm and interrupt the operation until the system is re-started by an operator input command.

If high level sensor 172 indicates the presence of liquid in top manifold 150 within the first purge cycle, a "drain" cycle will be activated at the conclusion of the first purge cycle. If liquid is detected in manifold 150 after the end of the first purge cycle, but before the end of the second purge cycle, the drain cycle will be activated in response to the electrical signal from sensor 172. The drain cycle is also set for predetermined period of time (e.g., five seconds). During the drain cycle, valve 198 is open to admit air into top manifold 150. Valve 114 is also open so that the liquid in sample chamber 112 drains downwardly through drain line 72. During the drain cycle, low level sensor 134 detects the presence of liquid in bottom manifold 116 and generates an electrical signal indicative thereof. When sample chamber 112 has been completely drained, low level sensor 134 will no longer detect the presence of liquid in bottom manifold 116 and the corresponding electrical signal will be discontinued. If the electrical signal from low level sensor 134 has not been discontinued within a period of time corresponding to two drain cycles (e.g., 10 seconds), a malfunction in the drain system is indicated and the system will log the event in memory, activate a malfunction alarm and interrupt the operation of the system until the system is restarted by an operator input command. If the electrical signal from sensor 134 is discontinued during the first drain cycle, the draining operation will continue until the end of the first drain cycle. If the electrical signal is discontinued after the first drain cycle, but before the end of the second drain cycle, the draining operation will be concluded when the electrical signal is discontinued.

At the conclusion of the drain cycle, CPU 314 will determine the zero offset voltage of the particular sensing circuit 236 or 246 which is "active" (i.e., the circuit whose LEL measurement is being used by CPU 314 to calculate the flash point). As previously indicated, the zero offset voltage is typically adjusted for a small offset voltage (e.g., 5 mv) when the bridge circuit is balanced. If the zero offset voltage of the active sensing circuit 236 or 246 exceeds a predetermined limit (e.g., 50 mv), CPU 314 will determine which one of the sensing circuits 236 or 246 is in use. If first bridge circuit 236 (Circuit A) is in use, the event will be logged in the system memory, a service alert alarm signal will be activated and CPU 314 will select second circuit 246 (Circuit B) as the "active" sensing circuit. Degradation in active filament 222 may result in the zero offset voltage exceeding the predetermined limit. By providing second circuit 246 as a backup, the system includes a redundancy feature, which minimizes system down time.

If second circuit 246 is already "active", an excessive zero offset voltage indicates a degraded condition of active filament 226. Because second circuit 246 is not used until a malfunction occurs in first circuit 236, the system will not switch back to first circuit 236, but rather will log the event in memory, activate a malfunction alarm and interrupt the operation of the system until it is re-started by a user input command.

If the zero offset voltage of first circuit 236 is acceptable or if the system switches to second circuit 246 (Circuit B) and the zero offset voltage of second circuit 246 is acceptable, the "fill" cycle will be initiated. During the fill cycle, sample chamber 112 is filled to a level at or just below top end 112b of reservoir 112a so that liquid does not enter tube 112c. Valves 104, 110 and 200 are open for a predetermined period of time (e.g., five seconds) and are then closed to stop the flow of liquid into sample chamber 112 when the liquid has reached the desired level in reservoir 112a. When reservoir 112a is filled with liquid, low level sensor 134 will detect the presence of liquid in bottom manifold 116. If low level sensor 134 does not generate a signal indicating the presence of liquid in bottom manifold 116 within a period of time corresponding to two fill cycles (e.g., 10 seconds), a malfunction in the fill system is indicated, whereupon the system will log the event in memory, activate a service alert alarm signal and interrupt the operation of the system until it is re-started by a user input command. During the fill cycle, valves 114, 130, 198 and 192 are closed.

If low level sensor 134 detects the presence of liquid in lower manifold 116 before the first fill cycle expires, filling will continue until the end of the first fill cycle. If sensor 134 detects liquid in manifold 116 after the first fill cycle, but before the end of the second cycle, the filling operation will be terminated when sensor 134 generates an electrical signal indicating the presence of liquid in manifold 116. When the filling operation is concluded, the sampling cycle is initiated. During the sampling cycle, valves 110 and 114 are closed and valves 130 and 192 are open to allow air to enter bottom manifold 116, whereby the liquid is aerated such that a combustible mixture of air and vapor is present in tube 112c. Valves 198 and 200 are also closed during the sampling cycle.

Vacuum pump 148 draws the combustible mixture upwardly through tube 112c into top manifold 150. The air-vapor mixture is discharged from top manifold 150 through line 162 and enters block 164 through line 194. The LEL of the sample is measured in block 164, as previously described. The vapor sampling cycle lasts for a predetermined period of time (e.g., 15 seconds). CPU 314 computes the flash point temperature of the sample based on the LEL, the temperature of the sample and the API gravity of the sample according to the equations set forth in the appropriate Table I or Table II. Table I is used when the product is fuel oil and Table II is used when the product is kerosine. The equation used to determine the flash point temperature varies depending upon the product temperature. LEL is measured as a percentage from 0–100%. The symbol "*" indicates the multiplication symbol and the symbol "E" represents base 10. The number following the E symbol in each equation represents the exponent of base 10, with a minus sign indicating a negative exponent and a plus sign indicating a positive exponent.

At the conclusion of the sampling cycle, sampling chamber 112 is drained according t the drain cycle previously described.

Figure 13:
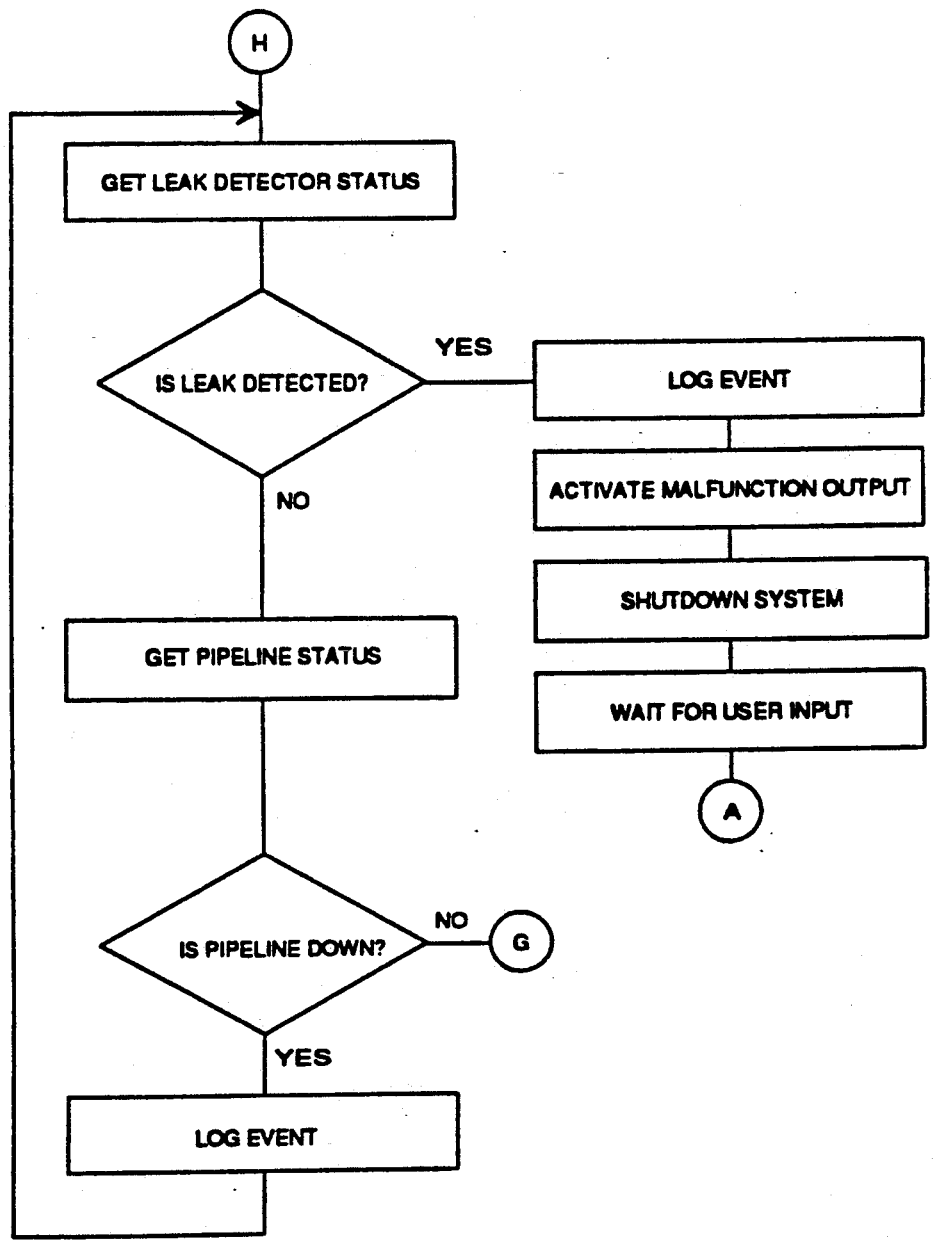
Figure 14:
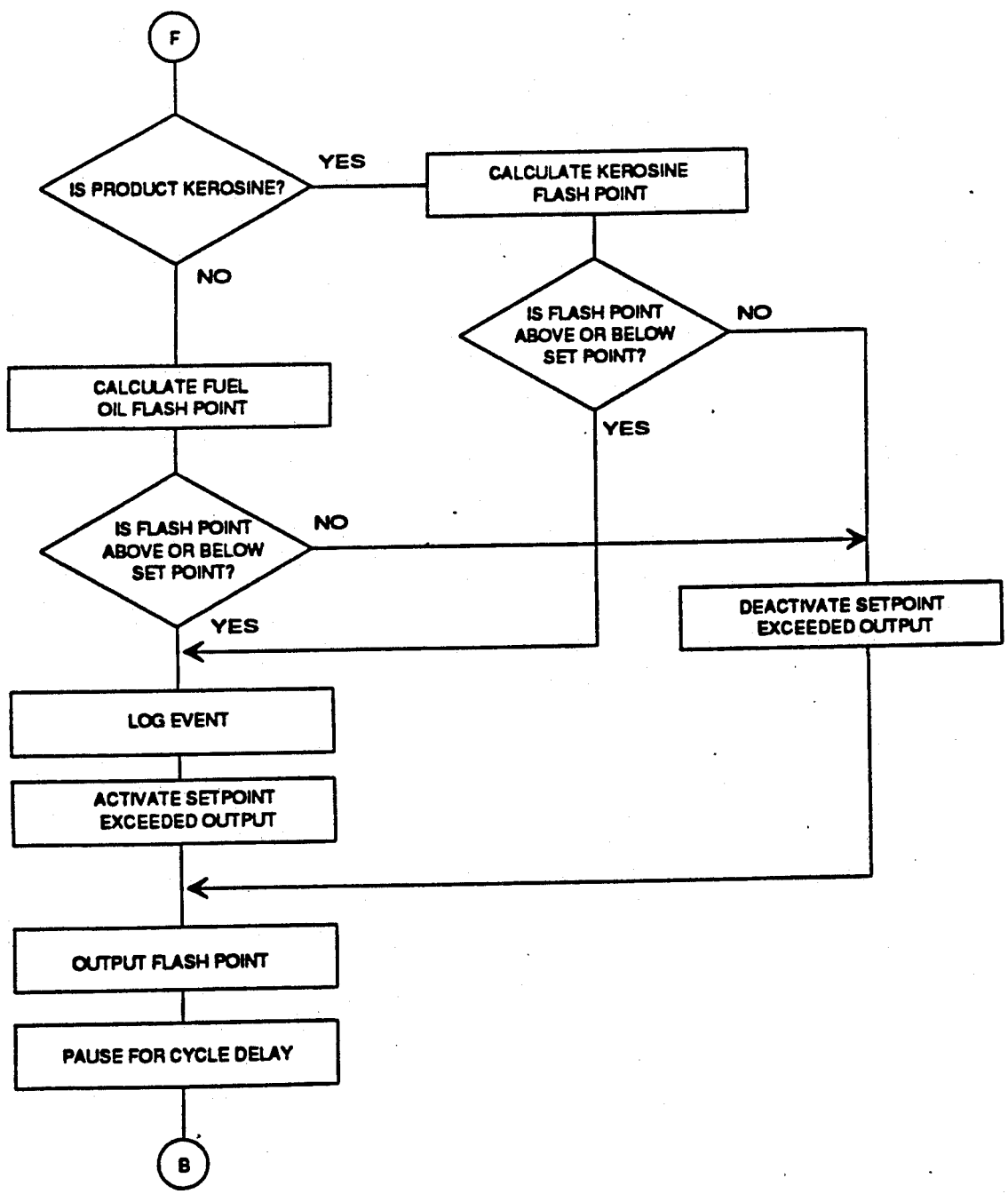

If the voltage output from the "active" bridge circuit 236 or 246 exceeds 50 mv, the vapor is considered to be "hot" (i.e., LEL is greater than 100%). If this condition occurs, the sampling cycle is interrupted and the system is drained. The event is logged in system memory and the flash point temperature is indicated as 0°. An alarm is activated indicating that the flash point temperature is outside the acceptable range. CPU 314 then determines, based on the API gravity if the product is gasoline. If the product is gasoline, the program will enter the loop depicted in FIG. 13 and will continue to monitor the status of float sensor 106 to determine the presence of leakage within housing 16 and will also monitor the status of pipeline 14. If a flow is detected in pipeline 14, CPU 314 will determine the type of product based on its API gravity. If the product is not gasoline, CPU 314 will determine whether the product is kerosine or fuel oil. If the flash point is above or below the applicable set point range, the event is logged in the system memory and an alarm is generated indicating that the flash point is outside the acceptable limits. If the flash point temperature is within acceptable limits, the flash point temperature is displayed on terminal 320 and is also transmitted to control room 318. The above-described process is then repeated for the next sample, beginning with the steps of monitoring float valve 106 for signs of leakage and pipeline 14 to determine the presence of flow within pipeline 14, as indicated in FIG. 10.

Although the invention has been described with reference to specific embodiments, the foregoing description is not intended to be construed in a limiting sense. Various modifications to the disclosed embodiment as well as alternative applications of the invention will be suggested to persons skilled in the art by the foregoing specification and by the drawings. It is therefore contemplated that the appended claims will cover any such modifications, applications or embodiments as fall within the true scope of the invention.

"TABLE I"

Fuel Oil 110 Deg F.
FLASHPNT = 1.70796662555+02
+($LEL^*$ 1.0735546687E−01)
+($LEL^{2*}$ −3.6041489092E−02)
+($LEL^{3*}$ 4.8107713656E−04)
+($LEL^{4*}$ −2.0229734668E−06)

Fuel Oil 100 Deg F.
FLASHPNT = 1.7198679552E+02
+($LEL^*$ −2.3097158279E−01)
+($LEL^{2*}$ −3.2504129960E−02)
+($LEL^{3*}$ 4.9492356910E−04)
+($LEL^{4*}$ −2.2831894022E−06)

Fuel Oil 90 Deg F.
FLASHPNT = 1.7285007931E+02
+($LEL^*$ −6.2551538159E−01)
+($LEL^{2*}$ −2.6943163870E−02)
+($LEL^{3*}$ 5.1762940527E−04)
+($LEL^{4*}$ −2.7362808445E−06)

Fuel Oil 80 Deg F.
FLASHPNT = 1.7466000406E+02
+($LEL^*$ −1.2857424724E+00)
+($LEL^{2*}$ −5.6657805707E−03)
+($LEL^{3*}$ 2.4758725767E−04)
+($LEL^{4*}$ −1.7113655236E−06)

Fuel Oil 70 Deg F.
FLASHPNT = 1.7520781990E+02
+($LEL^*$ −1.8056432422E+00)
+($LEL^{2*}$ 8.7366911441E−03)
+($LEL^{3*}$ 5.1787661311E−05)
+($LEL^{4*}$ −7.7360117991E−07)

Fuel Oil 60 Deg F.
FLASHPNT = 1.7489987823E+02
+($LEL^*$ −2.1853652534E+00)
+($LEL^{2*}$ 1.8417417883E−02)
+($LEL^{3*}$ −6.8798280156E−05)
+($LEL^{4*}$ −2.9863079198E−07)

Fuel Oil 50 Deg F.
FLASHPNT = 1.7426093085E+02
+($LEL^*$ −2.6764676344E+00)
+($LEL^{2*}$ 3.8064831899E−02)
+($LEL^{3*}$ −4.6624113022E−04)
+($LEL^{4*}$ 1.8782544151E−06)

Fuel Oil 40 Deg F.
FLASHPNT = 1.7374234822E+02
+($LEL^*$ −2.8708739725E+00)
+($LEL^{2*}$ 3.4272887091E−02)
+($LEL^{3*}$ −4.4101807314E−04)

"TABLE I"-continued

+($LEL^{4*}$ 1.8622978248E−06)

"TABLE II"

Kerosine 110 Deg F.
FLASHPNT = 1.4671166447E+02
+($LEL^*$ −8.3996141554E−01)
+($LEL^{2*}$ 1.0002487283E−02)
+($LEL^{3*}$ −1.1197543779E−04)
+($LEL^{4*}$ 3.84917−3513E−07)

Kerosine 100 Deg F.
FLASHPNT = 1.4879656280E+02
+($LEL^*$ −1.0670440486E+00)
+($LEL^{2*}$ 1.5199091958E−02)
+($LEL^{3*}$ −1.8189533686E−04)
+($LEL^{4*}$ 7.2449467670E−07)

Kerosine 90 Deg F.
FLASHPNT = 1.4422914379E+02
+($LEL^*$ −7.3746598413E−01)
+($LEL^{2*}$ 7.2514203296E−03)
+($LEL^{3*}$ −1.7159473808E−04)
+($LEL^{4*}$ 1.104155969E−06)

Kerosine 80 Deg F.
FLASHPNT = 1.4709426670E+02
+($LEL^*$ −7.8667023006E−01)
+($LEL^{2*}$ −8.4832487233E−03)
+($LEL^{3*}$ 1.7567288366E−04)
+($LEL^{4*}$ −8.7454831478E−07)

Kerosine 70 Deg F.
FLASHPNT = 1.4610036107E+02
+($LEL^*$ −7.9686092211E−01)
+($LEL^{2*}$ −1.8734070612E−02)
+($LEL^{3*}$ 4.0281344475E−04)
+($LEL^{4*}$ −2.2215152737E−06)

Kerosine 60 Deg F.
FLASHPNT = 1.4586250304E+02
+($LEL^*$ −1.2562636672E+00)
+($LEL^{2*}$ 1.3579755480E−03)
+($LEL^{3*}$ 7.2334812752E−05)
+($LEL^{4*}$ −6.2283689250E−07)

Kerosine 50 Deg F.
FLASHPNT = 1.4929035559E+02
+($LEL^*$ −1.9825448435E+00)
+($LEL^{2*}$ 2.5564130251E−02)
+($LEL^{3*}$ −3.1932362099E−04)
+($LEL^{4*}$ 1.3525924286E−06)

Kerosine 40 Deg F.
FLASHPNT = 1.4811265247E+02
+($LEL^*$ −2.2148179365E+00)
+($LEL^{2*}$ 2.9745901158E−02)
+($LEL^{3*}$ −3.9888388345E−04)
+($LEL^{4*}$ 1.791492881E−06)

What is claimed is:

1. Apparatus for determining flash point temperature of a liquid petroleum product being transported in a pipeline, said apparatus comprising, in combination:

first chamber means for storing a sample of the product;

product supply means communicating between the pipeline and said first chamber means for supplying the sample;

air supply means for introducing air into the sample such that a mixture of the air and vapor from the sample is present in said first chamber means;

second chamber means in fluid communication with said first chamber means;

suction means for drawing said mixture from said first chamber means into said second chamber means, said second chamber means including measuring means for measuring Lower Explosive Limit of said mixture;

temperature sensing means for measuring temperature of the sample;

density measuring means for measuring density of the sample relative to a predetermined reference; and processing means responsive to the measured Lower Explosive Limit of said mixture and to the measured temperature and density of the sample for determining the flash point temperature of the sample.

2. Apparatus of claim 1 wherein said measuring means includes a Wheatstone bridge circuit having first and second electrically resistive filaments located in respective first and second portions of said second chamber means, said first filament being exposed to said mixture when said mixture is in said second chamber means, the Lower Explosive Limit being directly proportional to a change in electrical resistance of said first filament when said first filament is exposed to said mixture, said second filament being a reference filament which is not exposed to said mixture.

3. Apparatus of claim 1 when said measuring means includes first and second Wheatstone bridge circuits, said first bridge circuit having first and second electrically resistive filaments located in respective first and second portions of said second chamber means, said first filament being exposed to said mixture when said mixture is in said chamber means, the Lower Explosive Limit being directly proportional to a change in the electrical resistance of said first filament when said first filament is exposed to said mixture, said second filament being a reference filament which is not exposed to said mixture, said second bridge circuit having third and fourth electrically resistive filaments located in respective third and fourth portions of said second chamber means, said third filament being exposed to said mixture when said mixture is in said second chamber means, the Lower Explosive Limit being directly proportional to a change in the electrical resistance of said third filament when said third filament is exposed to said mixture, said fourth filament being a reference filament which is not exposed to said mixture, said first bridge circuit being a primary measuring circuit such that said processing means is normally responsive to the Lower Explosive Limit measured by said primary measuring circuit for determining the flash point temperature, said second bridge circuit being a backup measuring circuit, said processing means being responsive to the Lower Explosive Limit measured by said backup measuring circuit upon the occurrence of a predetermined condition.

4. Apparatus of claim 3 wherein said predetermined condition corresponds to a value of the Lower Explosive Limit measured by said primary measuring circuit exceeding a predetermined maximum value of the Lower Explosive Limit.

5. Apparatus of claim 4 further including means for automatically disabling the operation of the apparatus when a value of the Lower Explosive Limit measured by said backup measuring circuit exceeds said predetermined maximum value of the Lower Explosive Limit.

6. Apparatus for determining flash point temperature of a liquid petroleum product being transported in a pipeline, said apparatus comprising, in combination:

first chamber means for storing a sample of the products, said first chamber means including a bottom reservoir for storing the sample and a tube extending upwardly from said reservoir, said first chamber means further including at least one baffle member located in said tube, said at least one baffle member having a plurality of apertures;

product supply means communicating between the pipeline and said first chamber means for supplying the sample;

air supply means for introducing air into the sample such that a mixture of the air and vapor from the sample is present in said first chamber means;

second chamber means in fluid communication with said first chamber means;

suction means for drawing said mixture from said first chamber means upwardly through said tube into said second chamber means, said apertures being adapted to allow said mixture to be drawn upwardly through said tube, said at least one baffle member substantially inhibiting liquid from being drawn upwardly through said tube, said second chamber means including measuring means for measuring Lower Explosive Limit of said mixture; and processing means responsive to the measured Lower Explosive Limit of said mixture for determining the flash point temperature of the sample.

7. Apparatus of claim 6 wherein said at least one baffle member includes first and second baffle members spaced apart within said tube, each of said first and second baffle members having a substantially cylindrical shape with a substantially greater width than height, an intermediate portion of each of said first and second baffle members being recessed relative to corresponding top and bottom portions thereof such that the corresponding intermediate portion is adapted to receive a resilient member, whereby each of said first and second baffle members is adapted for sealing engagement with an inner surface of said tube.

8. Apparatus for determining flash point temperature of a liquid petroleum product being transported in a pipeline, said apparatus comprising, in combination:

first chamber means for storing a sample of the product;

product supply means communicating between the pipeline and said first chamber means for supplying the sample;

air supply means for introducing air into the sample such that a mixture of the air and vapor from the sample is present in said first chamber means;

second chamber means in fluid communication with said first chamber means;

suction mean for drawing said mixture from said first chamber means into said second chamber means, said second chamber means including measuring means for measuring Lower Explosive Limit of said mixture;

top manifold means located above said first chamber means, said top manifold means having a generally vertical first passageway communicating with said first chamber means, said top manifold means further including first and second conduits, said first conduit communicating between said first passageway and said second chamber means, whereby said mixture is drawn through said first conduit into said second chamber means, said apparatus further including a purge line, said second conduit communicating between said first passageway and said purge line, whereby the sample is purged from said first chamber means upwardly through said top manifold means into said purge line;

bottom manifold means having a generally vertical second passageway communicating with said first chamber means, said bottom manifold means further including third and fourth conduits, said third conduit communicating between said product supply means and said second passageway, whereby the sample is supplied to said first chamber means through said bottom manifold means, said fourth conduit communicating between said air supply means and said second passageway, whereby air is supplied to said first chamber means through said bottom manifold means, said apparatus further including a drain line communicating with said first and second passageways to allow the sample to be drained from said first chamber means downwardly through said bottom manifold means, said first and second conduits being angled downwardly to enhance drainage of the product into said first passageway, said third and fourth conduits being angled downwardly to enhance drainage of the product into said second passageway.

9. A method of determining flash point temperature of a liquid petroleum product being transported in a pipeline, comprising the steps of:
providing apparatus having a first chamber and a second chamber in fluid communication with said first chamber;
drawing a sample of the product from the pipeline into said first chamber;
introducing air into the sample such that a combustible mixture of the air and vapor from the sample is present in said first chamber;
suctioning said mixture from said first chamber into said second chamber and allowing the vapor to ignite in said second chamber;
measuring Lower Explosive Limit of said mixture in said second chamber;
determining the flash point temperature of the sample in response to the measured Lower Explosive Limit; and
periodically repeating said drawing, said introducing, said suctioning, said measuring and said determining to continually monitor the flash point temperature of the product in the pipeline.

10. The method of claim 9 further including measuring the temperature and density of the sample in said first chamber, said determining including determining the flash point temperature in response to the measured Lower Explosive Limit, temperature and density.

11. The method of claim 10 further including purging the sample from said first chamber and said mixture from said second chamber prior to said drawing.

12. The method of claim 11 wherein said purging includes flushing product through said first chamber and drawing air through said second chamber.

13. The method of claim 12 including detecting the presence of liquid in a top portion of said first chamber and generating an electrical signal indicative thereof, said purging continuing for a predetermined time period if said electrical signal is generated during said first predetermined time period, said purging continuing after said first predetermined time period if said electrical signal is not generated during said first predetermined time period, until said electrical signal is generated or until a second predetermined time period has expired, whichever occurs first.

14. The method of claim 12 further including draining product from said first chamber after said purging and before said drawing.

15. The method of claim 14 further including detecting the presence of liquid in a bottom portion of said first chamber and generating an electrical signal indicative thereof, said draining continuing for a first predetermined time period if said electrical signal is discontinued during said first predetermined time period, said draining continuing after said first predetermined time period if said electrical signal is not discontinued during said first predetermined time period, until said electrical signal is discontinued or until a second predetermined time period has expired, whichever occurs first.

16. The method of claim 9 further including detecting the presence of liquid in a bottom portion of said first chamber and generating an electrical signal indicative thereof, said drawing continuing for a first predetermined time period if said electrical signal is generated during said first predetermined time period, said drawing continuing after said first predetermined time period if said electrical signal is not generated during said first predetermined time period, until said electrical signal is generated or until a second predetermined time period has expired, whichever occurs first.

17. The method of claim 9 wherein said measuring means includes first and second measuring means for measuring the Lower Explosive Limit of the sample, said first measuring means being normally used to measure the Lower Explosive Limit, said second measuring means being normally used as a backup, said method further including deactivating said first measuring means and activating said second measuring means upon the occurrence of a predetermined condition such that said second measuring means is used to measure the Lower Explosive Limit upon the occurrence of said predetermined condition.

18. The method of claim 9 further including generating an alarm signal when the flash point temperature is determined to be outside a predetermined range of acceptable flash point temperatures.

* * * * *